United States Patent
Milner et al.

(10) Patent No.: US 9,591,961 B2
(45) Date of Patent: *Mar. 14, 2017

(54) ROTATING CATHETER PROBE USING A LIGHT-DRIVE APPARATUS

(71) Applicant: Board of Regents, The University of Texas System, Austin, TX (US)

(72) Inventors: Thomas E. Milner, Austin, TX (US); Nathaniel J. Kemp, Concord, MA (US)

(73) Assignee: Board of Regents, The University of Texas System, Austin, TX (US)

( * ) Notice: Subject to any disclaimer, the term of this patent is extended or adjusted under 35 U.S.C. 154(b) by 39 days.

This patent is subject to a terminal disclaimer.

(21) Appl. No.: 13/785,262

(22) Filed: Mar. 5, 2013

(65) Prior Publication Data

US 2013/0245378 A1 Sep. 19, 2013

Related U.S. Application Data

(60) Division of application No. 12/902,092, filed on Oct. 11, 2010, now Pat. No. 8,401,610, which is a (Continued)

(51) Int. Cl.
*A61B 5/00* (2006.01)
*A61B 1/00* (2006.01)

(52) U.S. Cl.
CPC ........ *A61B 1/00163* (2013.01); *A61B 1/0011* (2013.01); *A61B 1/00172* (2013.01); (Continued)

(58) Field of Classification Search
CPC .................. A61B 1/00163; A61B 1/00172
See application file for complete search history.

(56) References Cited

U.S. PATENT DOCUMENTS

| 1,467,672 A | 9/1923 | Kaplan | 415/129 |
| 2,334,302 A | 11/1943 | Akins | 415/75 |

(Continued)

FOREIGN PATENT DOCUMENTS

| DE | 295 21 096 | 9/1996 | A61B 17/22 |
| EP | 0 147 192 | 7/1985 | A61B 17/22 |

(Continued)

OTHER PUBLICATIONS

Brezinski, M.E., et al., "Assessing atherosclerotic plaque morphology: comparison of optical coherence tomography and high frequency intravascular ultrasound" *Heart* 77: 397-403 (1997).

(Continued)

*Primary Examiner* — Rajeev Siripurapu
(74) *Attorney, Agent, or Firm* — J. Peter Paredes; David G. Rosenbaum; Rosenbaum IP, P.C.

(57) ABSTRACT

The invention is a rotating tip catheter-imaging probe where electromagnetic energy is delivered to the distal end of a catheter and converted to mechanical energy using a light drive apparatus. The mechanical energy is then used to rotate a mirror that redirects light in fixed pattern on a sample. The rotating element of the light drive apparatus contains vanes, which rotate about an axis and positioned with bearings to minimize friction. A chamber encompasses the rotating element and is set to a vacuum pressure. The rotational speed of the catheter tip can be controlled by varying the optical power delivered to the vanes, the vacuum pressure in the chamber, or by a braking mechanism applied to the rotating element. The vanes may be shaped in a particular geometry to increase forces on the vanes from thermally driven gas flow.

11 Claims, 2 Drawing Sheets

Related U.S. Application Data continuation of application No. 11/567,244, filed on Dec. 6, 2006, now Pat. No. 7,844,321, which is a continuation-in-part of application No. 10/548,982, filed as application No. PCT/US2004/012773 on Apr. 23, 2004, now Pat. No. 7,711,413.

(60) Provisional application No. 60/466,215, filed on Apr. 28, 2003.

(52) U.S. Cl.
CPC .......... *A61B 5/0066* (2013.01); *A61B 5/6852* (2013.01); *Y10T 29/49826* (2015.01)

(56) References Cited

U.S. PATENT DOCUMENTS

| | | | |
|---|---|---|---|
| 3,945,375 A | 3/1976 | Banko | 128/6 |
| 4,397,150 A | 8/1983 | Paller | 60/641.8 |
| 4,454,763 A | 6/1984 | Mahler | 73/639 |
| 4,648,892 A | 3/1987 | Kittrell et al. | 65/4.21 |
| 4,926,037 A | 5/1990 | Martin-Lopez | 250/205 |
| 5,176,141 A | 1/1993 | Bom et al. | 128/662.06 |
| 5,240,003 A | 8/1993 | Lancee et al. | 128/662.06 |
| 5,271,402 A | 12/1993 | Yeung et al. | 128/660.1 |
| 5,438,997 A | 8/1995 | Sieben et al. | 128/662.06 |
| 5,507,294 A | 4/1996 | Lum et al. | 128/662.06 |
| 5,509,418 A | 4/1996 | Lum et al. | 128/662.06 |
| 5,635,784 A | 6/1997 | Seale | 310/90.5 |
| 5,670,248 A | 9/1997 | Lazarov et al. | 428/304.4 |
| 5,776,556 A | 7/1998 | Lazarov et al. | 427/567 |
| 6,001,112 A | 12/1999 | Taylor | 606/159 |
| 6,069,698 A | 5/2000 | Ozawa et al. | 356/345 |
| 6,134,033 A | 10/2000 | Bergano et al. | 359/122 |
| 6,191,862 B1 | 2/2001 | Swanson et al. | 356/450 |
| 6,264,608 B1 | 7/2001 | Schatzle et al. | 600/439 |
| 6,357,998 B1 | 3/2002 | Rosefsky | 415/66 |
| 6,501,551 B1 | 12/2002 | Tearney et al. | 356/477 |
| 6,507,747 B1 | 1/2003 | Gowda et al. | 600/407 |
| 6,749,344 B2 | 6/2004 | Hamm et al. | 385/72 |
| 6,809,322 B2 | 10/2004 | Danilatos | 250/441.11 |
| 6,891,984 B2 | 5/2005 | Petersen et al. | 385/12 |
| 2001/0055462 A1 | 12/2001 | Seibel | 600/473 |
| 2002/0191911 A1* | 12/2002 | Ukrainczyk et al. | 385/33 |
| 2002/0198457 A1 | 12/2002 | Tearney et al. | 600/476 |
| 2003/0013952 A1 | 1/2003 | Iizuka et al. | 600/160 |
| 2003/0045785 A1 | 3/2003 | Diab et al. | 600/344 |
| 2006/0000215 A1 | 1/2006 | Kremen et al. | 60/721 |
| 2006/0001569 A1 | 1/2006 | Scandurra | 342/351 |

FOREIGN PATENT DOCUMENTS

| | | | |
|---|---|---|---|
| JP | 04-307047 | 10/1992 | A61B 8/12 |
| JP | 05-023336 | 2/1993 | A61B 8/12 |
| JP | 08-238239 | 9/1996 | A61B 8/00 |
| JP | 2000-070270 | 3/2000 | A61B 8/12 |
| JP | 2000-507860 | 6/2000 | A61F 7/00 |
| NL | 8700632 | 3/1987 | A61B 17/36 |
| WO | WO 99/44841 | 9/1999 | B44C 5/00 |
| WO | WO 2004/096049 | 11/2004 | A61B 6/00 |

OTHER PUBLICATIONS

Davies, M.J., "Plaque fissuring—the cause of acute myocardial infarction, sudden ischaemic death, and crescendo angina" *British Heart Journal* 53: 363-373 (1985).

Davies, M.J., et al., "Risk of thrombosis in human atherosclerotic plaques: role of extracellular lipid, macrophage, and smooth muscle cell content" *British Heart Journal* 69: 377-381 (1993).

Fujimoto, J.G., "Optical Coherence Tomography" *Encyclopedia of Optical Engineering*, 2: 1594 (2003).

Jang, I.K., et al., "Visualization of coronary atherosclerotic plaques in patients using optical coherence tomography: Comparison with intravascular ultrasound" *Journal of American College of Cardiology* 39(4): 604-609 (2002).

Little, W.C., et al., "The underlying coronary lesion in myocardial infarction: Implications for coronary angiography" *Clinical Cardiology* 14(11): 868-874.

Maxwell, J.C., "On stresses in rarified gases arising from inequalities of temperature" *Philosophical Transaction of the Royal Society of London* 170: 231-256 (1879).

Nissen, S., "Coronary angiography and intravascular ultrasound" *Am J Card* 87(4A): 15A-20A (2001).

Rabbani, R., et al., "Strategies to achieve coronary arterial plaque stabilization" *Cardiovascular Research* 41: 402-417 (1999).

Scandurra, M., "Enhanced radiometric forces" arXiv.org:physics, pp. 1-12 (2006) viewed on http://arXiv.org/abs/physics/0402011.

Villard, J., et al., "Use of a blood substitute to determine instantaneous murine right ventricular thickening with optical coherence tomography"*Circulation, Journal of the American Heart Association* 105: 1843-1849 (2002).

Wadsworth, "A computational study of radiometric phenomena for powering microactuators with unlimited displacements and large available forces" *Journal of Microelectromechanical Systems* 5(1): 59-65 (1996).

\* cited by examiner

ROTATING CATHETER PROBE USING A LIGHT-DRIVE APPARATUS

CROSS-REFERENCE TO RELATED APPLICATIONS

The present application is divisional of U.S. patent application Ser. No. 12/902,092, filed Oct. 12, 2010, which is a continuation of U.S. patent application Ser. No. 11/567,244, filed Dec. 6, 2006, now U.S. Pat. No. 7,844,321, which is a continuation-in-part of U.S. patent application Ser. No. 10/548,982, which was filed Sep. 7, 2005 and granted a U.S. national stage filing date of May 2, 2006, now U.S. Pat. No. 7,771,413, which claims priority to PCT International Patent Application No. PCT/US2004/012773, filed Apr. 23, 2004 and which claims priority to U.S. Provisional Patent Application Ser. No. 60/466,215, filed Apr. 28, 2003, all of which are hereby expressly incorporated by reference in their entireties.

STATEMENT OF GOVERNMENT SUPPORT

This invention was made with government support under Grant No. R01 EY016462 awarded by the National Institutes of Health. The government has certain rights in the invention.

BACKGROUND

The present invention relates generally to catheter probes, which direct optical energy for diagnostic or therapeutic purposes. More specifically, the invention relates to catheter probes using optical coherence tomography having a fixed or stationary optical imaging fiber.

Generally speaking, Optical Coherence Tomography ("OCT") is a technology that allows for non-invasive, cross-sectional optical imaging of biological media with high spatial resolution and high sensitivity OCT is an extension of low-coherence or white-light interferometry, in which a low temporal coherence light source is utilized to obtain precise localization of reflections internal to a probed structure along an optic axis. This technique is extended to enable scanning of the probe beam in the direction perpendicular to the optic axis, building up a two-dimensional reflectivity data set, used to create a cross-sectional gray-scale or false-color image of internal tissue backscatter.

OCT uses a superluminescent diode source or a tunable laser source emitting a 1300 nm wavelength, with a 50-250 nm bandwidth (distribution of wave length) to make in situ tomographic images with axial resolution of 2-20 µm and tissue penetration of 2-3 mm. OCT has the potential to image tissues at the level of a single cell. In fact, the inventors have recently utilized broader bandwidth optical sources, so that axial resolution is improved to 4 µm or less. With such resolution, OCT can be applied to visualize intimal caps, their thickness, details of their structure including fissures, the size and extent of the underlying lipid pool, and the presence of inflammatory cells. Moreover, near infrared light sources used in OCT instrumentation can penetrate into heavily calcified tissue regions characteristic of advanced coronary artery disease. With cellular resolution, application of OCT may be used to identify other details of the vulnerable plaque such as infiltration of monocytes and macrophages. In short, application of OCT can provide detailed images of a pathologic specimen without cutting or disturbing the tissue.

OCT can identify the pathological features that have been associated with vulnerable plaques. The distal end of the optical fiber is interfaced with a catheter for interrogation of the coronary artery during a heart catheterization procedure. The reflected light from the plaque is recombined with the signal from the reference mirror forming interference fringes (measured by a photovoltaic detector) allowing precise depth-resolved imaging of the plaque on a micron scale.

An OCT catheter to image coronary plaques have been constructed. (Jang I K, Bouma B E, Hang O H, et al. Visualization of coronary atherosclerotic plaques in patients using optical coherence tomography: comparison with intravascular ultrasound. JACC 2002; 39: 604-609, incorporated by reference herein). The prototype catheter consists of a single light source and is able to image over a 360-degree arc of a coronary arterial lumen by rotating a shaft that spins the optical fiber. Because the rotating shaft is housed outside of the body, the spinning rod in the catheter must rotate with uniform angular velocity so that the light can be focused for equal intervals of time on each angular segment of the coronary artery. Mechanical drag in the rotating shaft can produce significant distortion and artifacts in recorded OCT images of the coronary artery. Unfortunately, because the catheter will always be forced to make several bends between the entry point in the femoral artery to the coronary artery (e.g., the 180 degree turn around the aortic arch), uneven mechanical drag will result in OCT image artifacts As the application of OCT is shifted from imaging gross anatomical structures of the coronary artery to its capability to image at the level of a single cell, non-uniform rotation of the single fiber OCT prototype will become an increasingly problematic source of distortion and image artifact.

Consequently, endoscope type single channel OCT systems suffer from non-constant rotating speed that forms irregular images of a vessel target. See U.S. Pat. No. 6,134,003, which is hereby incorporated by reference. The use of rotating single mode fibers is prone to artifact production in the OCT image. The catheter will always be forced to make several bends from its entry in the femoral artery, to the 180-degree turn around the aortic arch, to its final destination in the coronary artery. All these bends will cause uneven friction on the rotary shaft, and uneven time distribution of the light on the entire 360-degree arch of the coronary artery. As the application of OCT is shifted from gross anatomical structures of the coronary artery to its capability to image at the level of a single cell, then non-uniform rotation of the single fiber OCT will become even a greater source of image artifact.

The present invention overcomes many of the problems associated with transducing motion in remote locations such as the distal end of an optical or ultrasonic imaging catheter inside the body, such as non-uniform rotational distortion (NURD) associated with direct mechanical actuation along a shaft, biocompatibility hazards associated with delivering substantial electrical currents or voltages to actuate motors or magnets, biocompatibility hazards and fluid dynamic limitations associated with using pressurized liquid or gas to actuate a turbine. The advantage of the present invention is that it delivers light to the internal volume of the thermal gradient, which is more efficient and less constrained.

SUMMARY OF THE INVENTION

The present invention is a rotating catheter probe where optical energy is delivered to the distal end of a catheter and converted to mechanical energy using a light drive apparatus. The light drive apparatus functions as a drive turbine to rotate a prism that redirects light onto a sample. The rotating element includes at least one vane member on a rotary axle, which is mounted on a posterior bearing and an anterior bearing to minimize friction. The rotating element is mounted in a vacuum chamber or capsule, which is, in turn, mounted at a distal end of a catheter and coaxial with an optical fiber, which passes down the length of the catheter. The rotational speed of the rotating element is proportional to the optical power applied to the vanes, and may be controlled by varying the optical power, varying the vacuum pressure in the chamber or capsule, or by a braking mechanism applied to the rotary axle. The vanes may be shaped in a particular geometry to maximize the thermal transpiration forces on the vanes.

Another embodiment of the invention is a method for delivering optical energy to a target for therapeutic or diagnostic purposes.

Another embodiment of the invention is a method of making a rotating tip catheter-imaging probe.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

In the accompanying figures, like elements are identified by like reference numerals among the several preferred embodiments of the present invention.

DETAILED DESCRIPTION OF THE INVENTION

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

The present invention relates to U.S. Provisional Patent Application Ser. No. 60/466,215 filed Apr. 28, 2003 (the '215 Provisional) and to PCT International Application No. PCT/US2004/012773 (the "773 PCT Application") filed Apr. 23, 2004, which designates the United States each of which is hereby incorporate by reference. The '215 Provisional and the '773 PCT Application disclose a catheter imaging probe for conducting optical coherence tomography in which light from a fixed or stationary optical fiber is directed onto a rotating prism or mirror. The prism or mirror is connected to a rotating rotor, which is driven by either fluid, such as liquids or gases, or by electromotive, or magnetomotive forces. As used in this application the term "catheter" is any device for bringing the probe within or without the body for scanning purposes, such as an endoscope, bronchoscope, laparoscope, otheoscope, catheter, or other similar devices.

Figure 1:
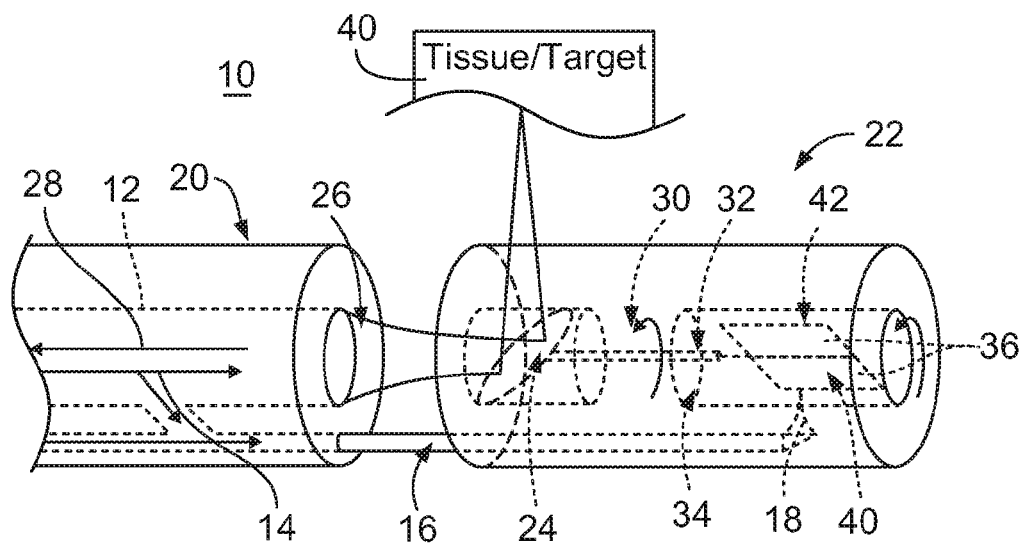
FIG. 1 is a diagram representation of the light drive apparatus coupled to an optical fiber.

Generally speaking, the present invention is a rotating catheter probe 10, where optical energy 14 is delivered to the distal end of a catheter housing 20 and converted to mechanical energy 30 using a light drive apparatus 22, as shown in FIG. 1. The light drive apparatus 22 rotates a prism 24, by thermal transpiration or thermal creep, resulting from the transduction of mechanical energy 30 from optical energy 14 applied to the light drive apparatus 22. An optical fiber 12 delivers the optical energy 14, which is also focused by a lensing element 26 onto the prism 24. When the light drive apparatus 22 rotates the prism 24, the prism 24 then redirects optical energy 14 away from the longitudinal axis of the catheter housing 20 and onto a target 40 while traversing a 360-degree arc. The optical fiber 12 does not rotate at all during the rotation of prism 24, and is able to receive backreflected light from the target 40. In one embodiment, the prism 24 is a mirrored prism, a totally-internally reflecting prism, or a dichroic reflector. The target 40 can be a blood vessel wall, or any target in which it is desired to direct optical energy. It should be appreciated that the light drive apparatus 22 can be used for other optical imaging systems or spectroscopic measurement devices, where optical energy is to be delivered and collected.

As shown in FIG. 1, the prism 24 is operably connected to the light drive apparatus 22 by a rotary axle 32, which extends distally from the prism 24. The distal end of the rotary axle 32 is operably connected to the light drive apparatus 22 through a chamber 34. Within the capillary tube 34, the light drive apparatus 22 includes a plurality of vanes 36 extending radially outward from the rotary axle 32. A first absorbent surface 42 of each vane 36 is coated with an energy absorbing material, such as black electrophoretic ink or powder black; while a second reflective surface 40 of each vane 36 is coated with an energy reflecting material, such as a metallization layer. A thermal isolating material can be used to isolate the absorbent surface 42 of the vane from the reflective surface 40, either by imposing it between the two surfaces or by applying a thermal insulator to the entire assembly prior to the coatings. It is to be understood that the first absorbent surface 42 and second reflective surface 40 provide a thermal gradient between the two surfaces. Any such material, surface, or coating providing a thermal gradient is encompassed by surfaces 40 & 42, as readily apparent to those skilled in the thermal arts.

The plurality of vanes 36, the axle 32, and a power transmitting fiber 16 comprises the light drive apparatus 22. The power transmitting fiber 16 transmits optical energy 14 to the absorbent surface 42 of the vanes 36 to induce thermal transpiration and consequently rotate the axle 32 and the prism 24. The power transmitting fiber 16 can include a reflecting element to transmit optical energy 14. Alternatively, a multi-mode fiber or a single-mode fiber can be used as the power transmitting fiber 16, which can be coupled to the optical fiber 12, as shown in FIG. 1. The chamber 34 holds the vanes 36 and the axle 32 at a specified pressure, optimal for thermal transpiration. The chamber 34 is evacuated to the appropriate vacuum level such that enough gas molecules are present to provide a transpiration force, but not enough for substantial drag forces to be incurred. Alternatively, a vacuum line is connected to the chamber 34 through the axle 32 during operation, such that the plurality of vanes 36 can adjust rotational speed 30 with minimal friction and distortion in rotation by varying the vacuum pressure of air molecules that create thermal transpiration. Alternatively, the rotational speed 30 of the light drive apparatus 22 can be controlled by varying the optical power 18 delivered to the vanes 36 or by a braking mechanism applied within the axle 32. The vanes 36 may be shaped in a particular geometry to increase forces on the vanes 36 from thermally driven gas flow. Alternatively, vanes may consist of a single screw-type vane.

"Thermal transpiration" and "thermal creep" are terms employed to describe the physical principal involved in the transduction of optical energy 14 into mechanical energy 30. When optical energy 14 impinges on the vanes 36, the axle 32 starts rotating due to a radiometric force. The absorbent surface 42 of each vane becomes hotter than the reflective surface 40, because of the different thermal absorption coefficients. The temperature or thermal gradient generates a force directed toward the colder reflective surface 42 as air molecules contained in the chamber 34 impinge on the vanes 36. Air molecules at a low density exert different pressures on the hot absorbent surface 42 and on the cold reflective surface 40.

Figure 2:
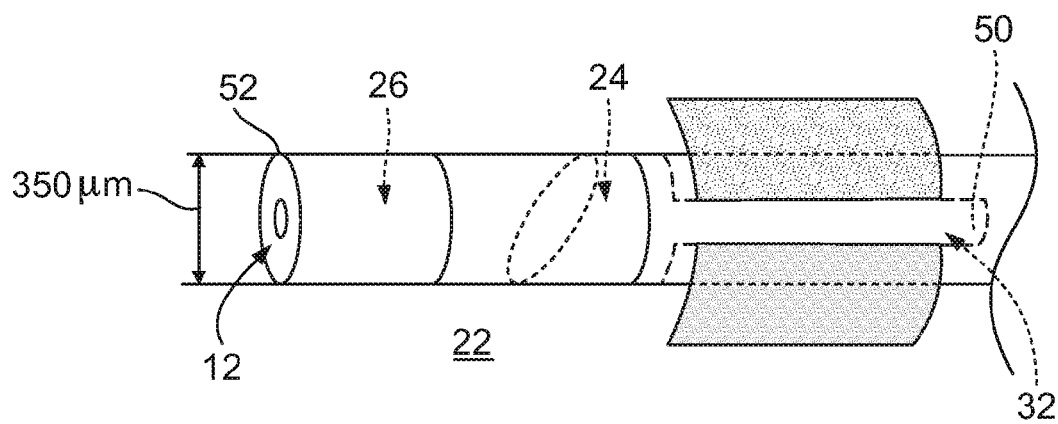
FIG. 2 is perspective view of the light drive apparatus for imparting rotational force to a prism in a catheter.
Figure 3:
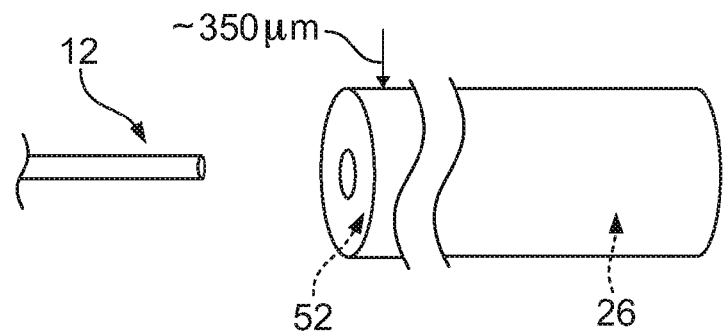
FIG. 3 is a perspective exploded view depicting a bearing and Gradient Index (GRIN) lens in accordance with a first embodiment of the present invention.

In order to promote efficient rotation of axle 32, the light drive apparatus 22 is positioned with an anterior bearing 52 and a posterior bearing 50 to minimize friction, as shown in FIG. 2. The anterior 52 and posterior 50 bearings for the light drive apparatus 22 are designed to interface with the single mode (SM) optical fiber 12 and the Gradient Index lens 26 ("GRIN lens"). Because the tip of the SM optical fiber 12 must be positioned with respect to the GRIN lens 26, the anterior bearing 52 is fabricated using LIGA to surround the SM optical fiber 12, as shown in FIG. 3. LIGA is a micromachining technology that employs high energy x-rays from a synchrotron to create high aspect ratio microstructures having micron to millimeter features. LIGA is an acronym for the German words for lithography, electroforming and molding. The GRIN lens 26 is operably bonded to the anterior bearing 52. The material for the anterior bearing 52 is selected based on the coefficient of the kinetic friction between the optical fiber 12 and LIGA fabricated bearing 52. The fiber 12 may be coated with a material that provides an effective contact surface with the LIGA fabricated bearing 52.

Figure 4:
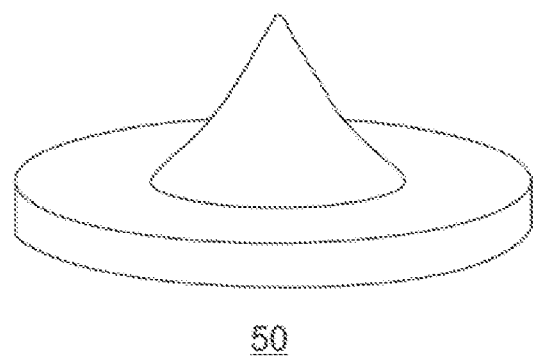
FIG. 4 is perspective view of an embodiment of the posterior bearing

The posterior bearing 50 must allow smooth, extremely low friction rotational motion of the axle 32 while preventing motion in the longitudinal or radial directions. In one embodiment, jewel or V-groove bearings made of hard and smooth surfaces such as sapphire will provide the most stability and less friction. Alternatively, magnetic and rolling bearings also can be used. The posterior bearing 50 can be fabricated using LIGA with material similar to those for the anterior bearing 52. In one embodiment, the design of the posterior bearing 50 is a conical pointed tip bearing, as shown in FIG. 4.

In operation, the GRIN lens 26 focuses energy 14 through a precisely controlled radial variation of the lens material's index of refraction from the optical axis to the edge of the lens 26. This allows a GRIN lens 26 with flat or angle polished surfaces to collimate light 14 emitted from an optical fiber 12 or to focus an incident beam into an optical fiber 12. The end faces of the GRIN lens 26 can be provided with an anti-reflection coating to avoid unwanted back reflection.

The light drive apparatus 22 generally comprises; (1) a GRIN lens 26 mounted onto an anterior bearing 52, (2) a dichroic reflector element 24 or a prism, (3) an axle 32 carrying radially extending vanes 36, and (4) a posterior bearing 50. Each of these sub-components is joined together to form a linear array of the light drive apparatus 22, as shown in FIGS. 2 & 3.

Figure 5:
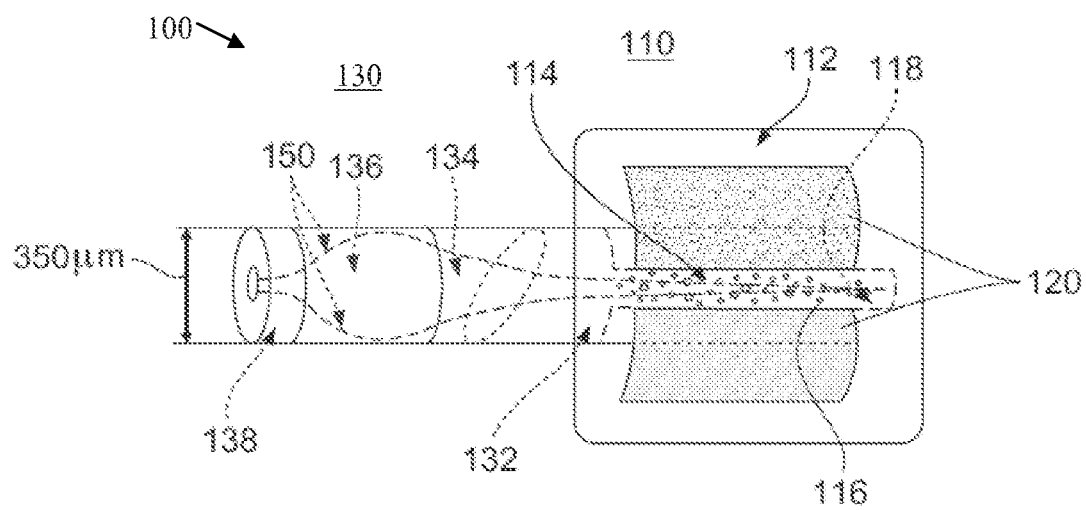
FIG. 5 is a perspective view of an embodiment of the light drive apparatus for imparting rotational force to a prism in a catheter illustrating light propagation through the device.

In another embodiment the invention, a rotating tip catheter imaging probe 10 comprises a light drive apparatus 22 including a rotating element 100 and optical components 130, as shown in FIG. 5. The rotating element 110 includes a capillary tube 112 and a plurality of radial vanes 120 bonded to the lumen of the capillary tube 112. The lumen of the capillary tube 112 is within an axle 118, while a scattering material 114 fills the lumen 116 of the capillary tube 112. The capillary tube 112 has an outer diameter of about 0.5 mm to about 1.0 mm in the outer diameter, while the lumen 116 has an inner diameter of about 50 microns. The capillary tube 112 is partially vacuum-sealed for optimal operation of thermal transpiration or thermal creep. The radial fins or vanes 120 have black and metallized surfaces bonded to proximal optical components 130 optimized for thermal transpiration or thermal creep, as discussed above.

The optical components 130 include a turbine input projection fiber 132, prism reflecting fiber 134, a gradient GRIN focusing fiber 136, and a source optical fiber 138, as shown in FIG. 5. The GRIN focusing fiber 136 is rotatably coupled to the axle 118, while the input projection fiber 132 is optically coupled to the lumen 116 of the axle 118. In operation, energy 150 is transmitted from the source fiber 138 and is used to heat the plurality of vanes 120 provided along the axle 118 via the scattering material 114, which deflects the optical energy to the plurality of vanes 120 within the capillary tube 112. The scattering material 114 is selected such that the light incident from the end will scatter radially outward. The scattering coefficient of the material filling the inner lumen may be chosen so that scattering is of proper strength to allow light propagation along the axial length of the turbine. The stock length of the capillary tube 112 may be about 10-100 mm or longer. Alternatively, the glass of the capillary tube 112 can be doped with impurities to case scattering. The impurities can be metal or dielectric particles.

Figure 6:
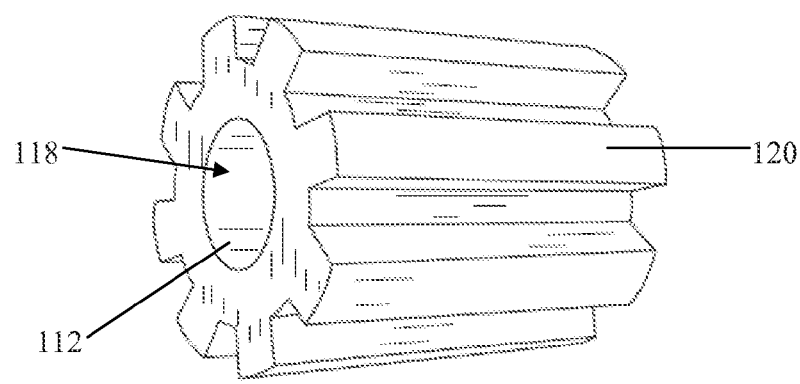
FIG. 6 is a perspective view of an embodiment of a rotor drive in accordance with the present invention.

The radial fins or vanes 120 will run along the entire length of the axle 118 of the capillary tube 112, as shown in FIG. 6. The number of fins or vanes 120 will be at least one. In one embodiment, fin or vane 120 geometry is broader at the base and narrows toward the edge of the fin or vane. The metal selected to metallize the surface of the capillary tube 112 should be highly reflective at the drive wavelength. Alternatively, a single vane 120 may consist of a screw-type design to provide for efficient rotation by thermal transpiration.

Alternatively, the capillary tube 112 is bonded to encompass all of the optical components 130, which include the turbine-input projection fiber 132, a prism reflecting fiber 134, and a GRIN focusing fiber 136, as shown in FIG. 5. The entire assembly is positioned and mounted in a partial vacuum-sealed capillary tube 112 and then positioned next to the terminus of the source optical fiber 138. The optical energy is input axially to the rotating element 110 and can be collinear with the probe light energy, but only at a different wavelength. The rotating element 110 can be separated from the probe light by a dichroic film at the deflecting interface.

The invention also includes a method for directing optical energy for diagnostic or therapeutic purposes comprising, directing energy to a rotatably mounted vane member within a vacuum sealed chamber, coupling the vane member to a rotatably mounted reflecting element, rotating the vane member by operation of thermal transpiration as to rotate the reflecting element, and directing energy to the reflecting element. It should be appreciated that the light drive apparatus can be used in other optical imaging systems and spectroscopic measurements where optical energy is required to be delivered and collected.

The invention also comprises a method of manufacturing a light drive turbine comprises filling the inner lumen of a capillary tube, of about 0.5-1.0 mm in outer diameter and about 50 microns of inner diameter and about 10 mm in length, with a scattering material; mounting the capillary tube in a jig; laser machining radial vanes along the entire length of the capillary tube; metallizing the entire surface of the capillary tube; bonding a wire to the metal at a position on the capillary tube; removing the metal on one side of the vane; applying a potential to the bonded wire; depositing black positively charged electrophoretic ink on the vane surface; cutting the capillary tube into segments of about 1-2 mm; bonding these segments to proximal segments comprised of a turbine-input projection fiber, a prism reflecting fiber, and a GRIN focusing fiber; mounting the assembly in a partial vacuum sealed capillary tube; and providing proximal and distal bearings.

The wire bonded to the metal surface can be bonded anywhere on the entire surface of the capillary tube as long as it is convenient and accessible. The wire is used to vary the electrical potential in the step of depositing the black color.

Removing the metal on one side of the vane in the removal step can be achieved with laser machining or a spatially selective chemical etch. This results in the vane or fin which is metallized entirely, except for the regions on one side of each fin near the edge of the fin.

In the step of applying potential to the bonded wire, the metallized surface becomes electropositive or electronegative depending on the type of electrophoretic ink used. In one embodiment, a black electropositive ink is used in a deposition step, either chemical or vacuum deposition. When the metal film is charged electropositive, the black electropositive ink binds to the exposed glass surface.

EXAMPLE 1

Already, simulations of the imaging probe's turbine have been run using a Direct Simulation Monte Carlo (DSMC), with the initial conditions modified from a "Sone Thermal Creep" example to reflect the preferred embodiment of the turbine's vanes. This simulation is run at a very low temperature, and depicted thermal creep using the preferred embodiment of the vanes.

EXAMPLE 2

It is feasible to use the DSMC with modified initial conditions to run a simulation wherein the reference temperature is about 310 K (roughly the temperature within a human body), and starting both sides of the vane, absorbent and reflective, at the same 310 K temperature. This simulation demonstrates roughly the expected working conditions of the probe, and that there is enough force generated by thermal transpiration to rotate the probe assembly alone, without rotating the fiber running the length of the catheter.

It should be understood that while this invention has been described herein in terms of specific embodiments set forth in detail, such embodiments are presented by way of illustration of the general principles of the invention, and the invention is not necessarily limited thereto. Certain modifications and variations in any given material or process step will be readily apparent to those skilled in the art without departing from the true spirit and scope of the present invention, and all such modifications and variations should be considered within the scope of the claims that follow. The contents of the articles, patents, and patent applications, and all other documents mentioned or cited herein, are hereby incorporated by reference in their entirety to the same extent as if each individual publication was specifically and individually indicated to be incorporated by reference.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. A method of making an optical imaging device, comprising the steps of:
   providing a body having a central longitudinal lumen extending from a proximal end to a distal end of the body;
   disposing an optical conduit within the central longitudinal lumen of the body and operably coupled with an optical imaging device;
   disposing a rotating reflecting element at a distal end of the body in optical communication with the optical conduit;
   positioning a gradient index lens proximal to the rotating reflecting element and in optical communication between the optical conduit and the rotating reflecting element;
   mounting a plurality of vane members on a central rotary axle of the rotating reflecting element, wherein each of the plurality of vane members comprising an energy absorbing surface and an energy reflecting surface to provide for a thermal gradient when optical energy impinges on the plurality of vane members, and the rotating reflecting element further comprises a capillary tube having an inner lumen in optical communication with the optical conduit and the plurality of vane members are provided along the inner lumen, wherein the inner lumen includes a light scattering material for directing incident light toward the energy reflecting surface and the energy absorbing surface; and selecting a scattering coefficient for the light scattering material that scatters light incident radially outward.

2. A method of making an optical imaging device, comprising the steps of:
   providing a body having a central longitudinal lumen extending from a proximal end to a distal end of the body;
   disposing an optical conduit within the central longitudinal lumen of the body and operably coupled with an optical imaging device;
   disposing a rotating reflecting element at a distal end of the body in optical communication with the optical conduit, the rotating reflecting in optical communication with the optical conduit;

positioning a gradient index lens proximal to the rotating reflecting element and in optical communication between the optical conduit and the rotating reflecting element; and mounting a plurality of vane members on a central rotary axle disposed within an optically transparent tube, wherein each of the plurality of vane members having an energy absorbing surface and an energy reflecting surface to provide for a thermal gradient when optical energy impinges on the plurality of vane members, wherein the light drive apparatus is made by the steps of:

filling the optically transparent tube with a light scattering material having a scattering coefficient sufficient to propagate light along an entire longitudinal length of the optically transparent tube and doping the glass of the optically transparent tube with impurities to encase scattering within the optically transparent tube;

forming the plurality of radial vanes along the longitudinal length of the optically transparent tube;

metallizing the optically transparent tube and plurality of radial vanes with a light reflective metal;

removing the metallizing of the optically transparent tube on at least a portion of one side of each of the plurality of radial vanes;

applying an electrical charge to the metallization; and depositing a charged energy absorbing material having a charge opposite the applied electrical charge to the metallization to preferentially bind the energy absorbing material to areas where metallization was removed.

3. The method of claim 1, further comprising vacuum sealing the capillary tube.

4. The method of claim 3, further comprising coupling an optical energy input axially through the rotating reflecting element and including a first optical energy, where the first optical energy is collinear with a second optical energy only at a different wavelength.

5. The method of claim 4, further comprising separating the rotating reflecting element using a dichroic film at a deflecting interface.

6. The method of claim 5, further comprising laser machining radial vanes along the entire length of the capillary tube.

7. The method of claim 6, further comprising interfacing the gradient index lens with an anterior bearing and interfacing the optical conduit with a posterior bearing; and fabricating the anterior bearing with high energy x-rays from a synchrotron to create high aspect ratio microstructures.

8. The method of claim 7, further comprising selecting the material for the anterior bearing based on the coefficient of kinetic friction between the optical conduit and the anterior bearing.

9. The method of claim 8, wherein the posterior bearing is a V-groove bearing made of sapphire.

10. The method of claim 9, further comprising providing an anti-reflection coating on the end faces of the gradient index lens to avoid back reflection.

11. The method of claim 2, wherein the removing metallization is selected from laser machining and a spatially selective chemical etch.

* * * * *